United States Patent
Liu et al.

(10) Patent No.: US 11,803,939 B2
(45) Date of Patent: Oct. 31, 2023

(54) UNSUPERVISED INTERSLICE SUPER-RESOLUTION FOR MEDICAL IMAGES

(71) Applicant: Shanghai United Imaging Intelligence Co., LTD., Shanghai (CN)

(72) Inventors: Yikang Liu, Cambridge, MA (US); Zhang Chen, Cambridge, MA (US); Xiao Chen, Cambridge, MA (US); Shanhui Sun, Cambridge, MA (US); Terrence Chen, Cambridge, MA (US)

(73) Assignee: Shanghai United Imaging Intelligence Co., LTD., Shanghai (CN)

( * ) Notice: Subject to any disclaimer, the term of this patent is extended or adjusted under 35 U.S.C. 154(b) by 363 days.

(21) Appl. No.: 17/242,473

(22) Filed: Apr. 28, 2021

(65) Prior Publication Data
US 2022/0366535 A1 Nov. 17, 2022

(51) Int. Cl.
| | |
|---|---|
| *G06T 19/20* | (2011.01) |
| *G06T 3/40* | (2006.01) |
| *G16H 30/20* | (2018.01) |
| *G16H 30/40* | (2018.01) |
| *G06T 11/00* | (2006.01) |
| *G06N 3/088* | (2023.01) |

(52) U.S. Cl.
CPC ........... *G06T 3/4053* (2013.01); *G06N 3/088* (2013.01); *G06T 3/4046* (2013.01); *G06T 11/006* (2013.01); *G16H 30/40* (2018.01)

(58) Field of Classification Search
None
See application file for complete search history.

(56) References Cited

U.S. PATENT DOCUMENTS

| | | | |
|---|---|---|---|
| 6,984,981 B2 | 1/2006 | Tamez-Peña et al. | |
| 8,094,900 B2 | 1/2012 | Steines et al. | |
| 11,092,659 B2* | 8/2021 | Amthor | G01R 33/4828 |
| 11,353,530 B2* | 6/2022 | Riederer | A61B 5/7257 |
| 2007/0031019 A1* | 2/2007 | Lesage | G06T 7/60 382/173 |
| 2008/0317315 A1* | 12/2008 | Stemmer | G01R 33/56509 382/131 |
| 2013/0034282 A1* | 2/2013 | Kaufman | G06T 7/0014 382/128 |
| 2023/0043026 A1* | 2/2023 | Duan | G06V 10/22 |
| 2023/0118907 A1* | 4/2023 | Iguchi | H04N 19/119 375/240.02 |

OTHER PUBLICATIONS

Van Overloop et al., "Experimental comparison of 2D and 3D wavelet image compression methods for medical image sets," Proc. SPIE 3335, Medical Imaging 1998: Image Display, (Jun. 26, 1998) (Year: 1998).*

Rehman et al., "Texture based localization of a brain tumor from MR-images by using a machine learning approach," Medical Hypotheses 141 (2020) 109705 (Year: 2020).*

* cited by examiner

*Primary Examiner* — Soo Shin
(74) *Attorney, Agent, or Firm* — Ziegler IP Law Group

(57) ABSTRACT

An unsupervised machine learning method with self-supervision losses improves a slice-wise spatial resolution of 3D medical images with thick slices, and does not require high resolution images as the ground truth for training. The method utilizes information from high-resolution dimensions to increase a resolution of another desired dimension.

20 Claims, 2 Drawing Sheets

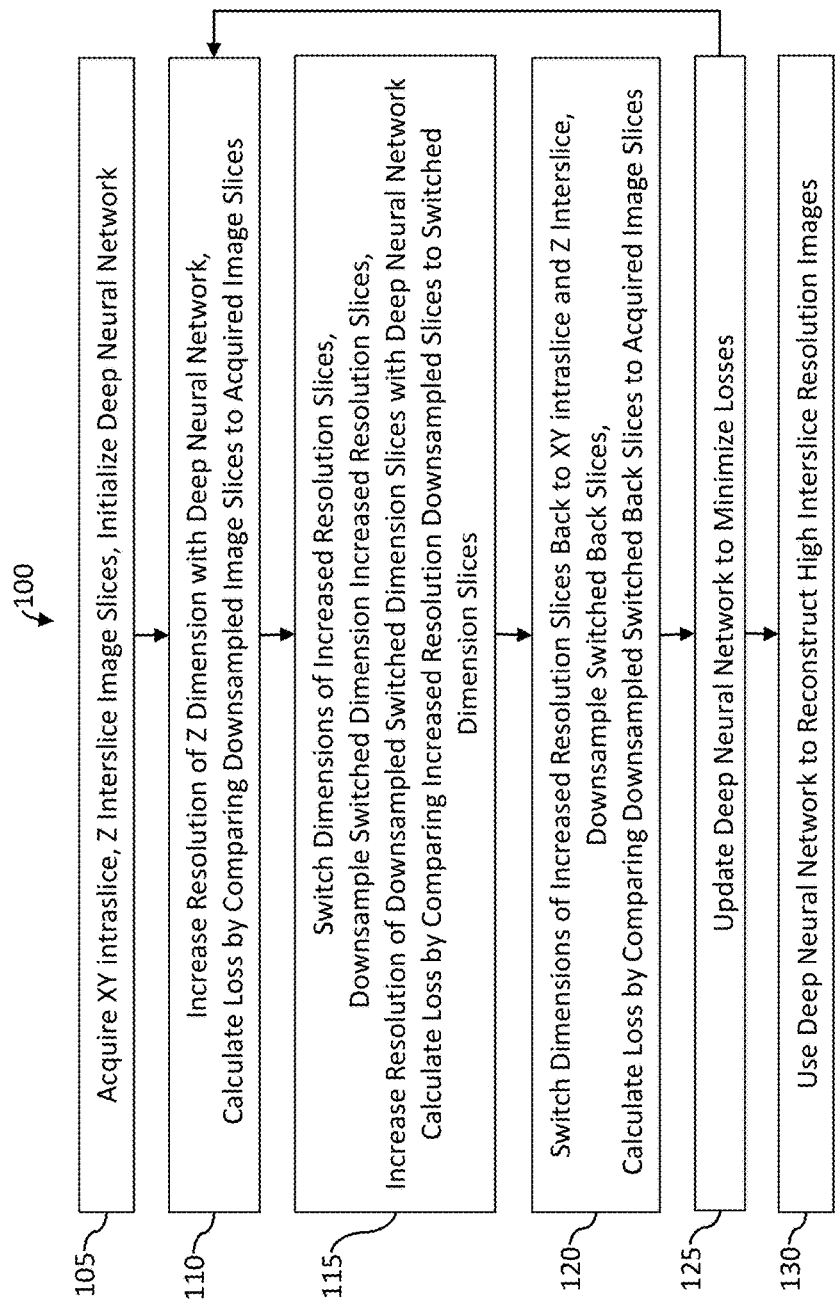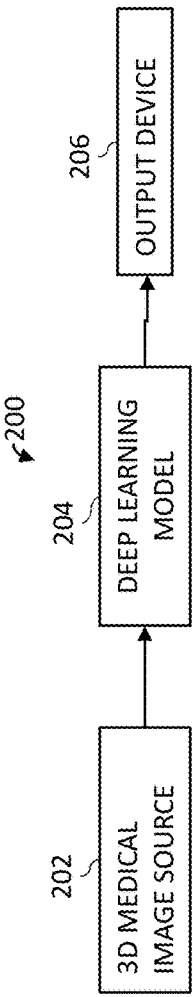

UNSUPERVISED INTERSLICE SUPER-RESOLUTION FOR MEDICAL IMAGES

BACKGROUND

The aspects of the present disclosure relate generally to 3D medical imaging, and in particular to using deep learning to improve the resolution of 3D medical images.

3D medical images, for example, magnetic resonance imaging, computed tomography, and microscopy, are generally acquired with relatively large dimensions and resulting low resolution in the interslice direction due to limitations of acquisition time and equipment in clinical environments. Given these relatively large dimensions and low resolution, downstream applications such as 3D rendering for better image comprehension and quantitative analysis, for example for analysis of certain anatomical structure volumes, usually provide unsatisfactory results.

SUMMARY

It would be advantageous to provide a method and system that provides increased resolution in the interslice direction without human intervention.

The disclosed embodiments are directed to an unsupervised machine learning method and system with self-supervision losses that improves a slice-wise spatial resolution of 3D medical images with thick slices, and does not require high resolution images as the ground truth for training. The model utilizes information from high-resolution dimensions to increase a resolution of another desired dimension.

In another aspect, the disclosed embodiments are directed to a method including acquiring first 3D image slices with interslice resolutions lower than intraslice resolutions, upsampling the first 3D image slices to produce second 3D image slices with increased interslice resolutions by using an adjustable mathematical mapping, downsampling the second 3D image slices, calculating first self-supervision losses by measuring differences between the downsampled image slices and the first 3D image slices, modifying the mathematical mapping to minimize the first self-supervision losses, using the modified mathematical mapping to modify the second 3D image slices; and providing the modified second 3D image slices to a user through a user interface.

The method may include downsampling the modified second 3D image slices to dimensions of the first 3D image slices.

The method may include switching dimensions of the modified second 3D image slices to produce third 3D image slices, downsampling the third 3D image slices to dimensions of the first 3D image slices, upsampling the downsampled third 3D image slices to produce fourth 3D image slices using the adjustable mathematical mapping, calculating second self-supervision losses by measuring differences between the third and fourth 3D image slices, and adjusting the adjustable mathematical mapping to minimize the second self-supervision losses.

Switching dimensions of the second 3D image slices may produce the third 3D image slices with interslice resolutions matching the intraslice resolutions of the first 3D images.

Upsampling the downsampled third 3D image slices may produce the fourth 3D image slices with dimensions of the third 3D image slices.

The method may still further include switching dimensions of the fourth 3D image slices to produce fifth 3D image slices, downsampling the fifth 3D image slices to produce sixth 3D image slices, calculating third self-supervision losses by measuring differences between the sixth 3D image slices and the first 3D image slices, adjusting the mapping to minimize the second and third self-supervision losses, using the optimized mapping to generate second 3D image slices from the first 3D image slices; and providing the second 3D image slices to a user through a user interface.

Switching dimensions of the fifth 3D image slices may produce the sixth 3D image slices with intraslice and interslice axes matching intraslice and interslice axes of the first 3D image slices.

Downsampling the fifth 3D image slices may produce the sixth 3D image slices with dimensions of the first 3D image slices.

The method may further include using a deep neural network to formulate the mathematical mapping for upsampling the first 3D image slices to the second 3D image slices and a computational framework to optimize the deep neural network by switching dimensions of the second and fourth image slices, downsampling the third and the fifth image slices, computing the first, second, and third self-supervision losses, and adjusting the deep neural network to minimize the losses.

The deep neural network may include one or more gated recurrent units, long short term memory networks, fully convolutional neural network models, generative adversarial networks, back propagation neural network models, radial basis function neural network models, deep belief nets neural network models, and Elman neural network models.

In another aspect the disclosed embodiments are directed to a system including a source of first 3D image slices with interslice resolutions lower than intraslice resolutions, a deep neural network to upsample the first 3D image slices to the second 3D image slices and upsample the downsampled third 3D image slices to the fourth 3D image slices, and a computational framework to optimize the deep neural network by switching dimensions of the second and fourth image slices, downsampling the third and the fifth image slices, computing the first, second, and third self-supervision losses, and adjusting the deep neural network to minimize the losses, and the system may further include a user interface for providing the second 3D image slices produced by the optimized deep neural network to a user.

These and other aspects, implementation forms, and advantages of the exemplary embodiments will become apparent from the embodiments described herein considered in conjunction with the accompanying drawings. It is to be understood, however, that the description and drawings are designed solely for purposes of illustration and not as a definition of the limits of the disclosed invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

In the following detailed portion of the present disclosure, the invention will be explained in more detail with reference to the example embodiments shown in the drawings. These embodiments are non-limiting exemplary embodiments, in which like reference numerals represent similar structures throughout the several views of the drawings, wherein:

FIG. 1 illustrates a general overview of a workflow 100 for generating interslice super-resolution for medical images with unsupervised deep learning;

FIG. 2 illustrates a schematic block diagram of an exemplary system incorporating aspects of the disclosed embodiments;

DETAILED DESCRIPTION

Figure 3:
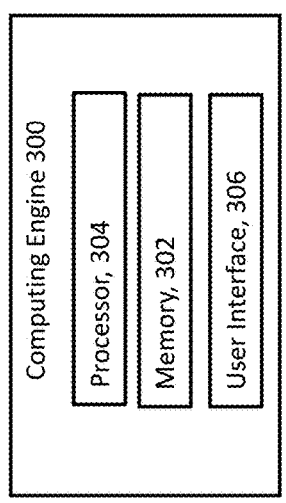
FIG. 3 illustrates an exemplary architecture of a computing engine that may be used to implement the disclosed embodiments.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The disclosed embodiments are directed to a method and system that utilize deep learning to recover isotropic images from images with relatively large interslice dimensions, which are able to generate sharp patterns in the interslice direction and improve the quality of downstream tasks with little or no human intervention.

It may be possible to implement deep learning methods that utilize supervised learning to improve the resolution of 3D medical images, where a deep learning model learns to generate high resolution images using pairs of low resolution images for training. However, generating high resolution images for training is costly, and in some circumstances may even be infeasible. The disclosed embodiments are directed to a deep learning method utilizing unsupervised learning for increasing interslice image resolution which does not require high resolution images as a training ground truth.

For purposes of the disclosed embodiments, the acquired 3D medical images have intraslice X and Y dimensions with relatively high resolution and interslice Z dimensions with a resolution lower than the X and Y dimensions, and the disclosed embodiments are directed to increasing the resolution of the interslice Z dimensions, also referred to as achieving super-resolution. While the disclosed embodiments are described in the context of 3D medical image slices, it should be understood that the disclosed embodiments may utilize any suitable 3D images. Due to the difficulty of acquiring ground truth high-resolution images, the disclosed embodiments utilize an unsupervised training strategy, where the deep learning model is trained on low-resolution datasets with self-supervision losses without human intervention.

Various operations of the system and method for achieving super-resolution are described in the context of utilizing a deep learning model, and it should be understood that individual deep learning models may be utilized for various operations, different deep-learning models may be used for combinations of various operations, or a single deep learning model may be utilized for all the operations.

FIG. 1 illustrates a general overview of a workflow 100 for generating interslice super-resolution for medical images with unsupervised deep learning. Original image slices $I_{LR}$ with intraslice X and Y dimensions and interslice Z dimensions may be acquired, and a deep neural network $f_\theta$ with parameters $\theta$ that increases the resolution of the image slices in the Z dimension may be initialized at block 105. The increased resolution image slices $I_{HR}$ may be downsampled to the original image slice dimensions, and the downsampled image slices $\widetilde{I_{HR}}$ may be compared with the original image slices $I_{LR}$ to calculate first self-supervision losses $L_1$ at block 110:

$$L_1 = m(\widetilde{I_{HR}}, I_{LR})$$

$$\widetilde{I_{HR}} = ds(f_\theta(I_{LR})),$$

where m is a metric measuring the difference between $\widetilde{I_{HR}}$ and $I_{LR}$ and ds is a downsampling operation.

The dimensions of the increased resolution image slices may be switched to produce image slices with interslice dimensions in the X dimensions $S_{HR,X}$ and to produce image slices with interslice dimensions in the Y dimensions $S_{HR,Y}$, the switched dimension increased resolution image slices may be downsampled to the original image slice sizes in the respective X and Y dimensions $\widetilde{S_{HR,}}$, the resolution of the downsampled switched dimension image slices may be increased to the resolutions of the switched dimension increased resolution image slices by the deep neural network $f_\theta$, and may be compared with the switched dimension increased resolution slices $S_{HR}$ to calculate second self-supervision losses $L_2$ at block 115:

$$L_2 = m(S'_{HR}, S_{HR})$$

$$S'_{HR} = f_\theta(\widetilde{S_{HR}}) \quad (2)$$

The dimensions of the switched dimension increased resolution image slices $S'_{HR}$ may be switched back to intraslice X and Y dimensions and interslice Z dimensions $S''_{HR}$, the switched back increased resolution image slices may be downsampled, and may be compared with the original image slices $I_{LR}$ to calculate third self-supervision losses $L_3$ at block 120:

$$L_3 = m(ds(S''_{HR}), I_{LR}) \quad (3)$$

The deep neural network may be updated iteratively to minimize the self-supervision losses (Eq. 1-3) that serve as constraints under which the network learns a mapping from low resolution image slices to high resolution image slices with consistent features as in the low resolution image slices at block 125.

The deep neural network may be used to provide image slices of high inter-slice resolution with low resolution image slices as inputs after being optimized to minimize the self-supervision losses (Eq. 1-3) at block 130.

FIG. 2 illustrates a schematic block diagram of an exemplary system 200 incorporating aspects of the disclosed embodiments. The system 200 may include a source of 3D medical image slices 202 with interslice Z dimensions having a lower resolution than intraslice X and Y dimensions, at least one deep learning model 204 for performing the operations disclosed herein, and one or more user interfaces, or other output devices 206 for providing the super-resolution image slices to one or more users. It should be understood that the components of the system 200 may be implemented in hardware, software, or a combination of hardware and software.

FIG. 3 illustrates an exemplary architecture of a computing engine 300 that may be used to implement the disclosed embodiments. The computing engine 300 may include computer readable program code stored on at least one computer readable medium 302 for carrying out and executing the process steps described herein. The computer readable program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The computer readable program code may execute entirely on the computing engine 300, partly on the computing engine 300, as a stand-alone software package, or partly or entirely on a remote computer or server, such as a cloud service.

The computer readable medium 302 may be a memory of the computing engine 300. In alternate aspects, the computer readable program code may be stored in a memory external to, or remote from, the computing engine 300. The memory may include magnetic media, semiconductor media, optical media, or any media which is readable and executable by a computer. The computing engine 300 may also include a computer processor 304 for executing the computer readable program code stored on the at least one computer readable medium 302. In at least one aspect, the computing engine 300 may include one or more input or output devices, generally referred to as a user interface 306 which may operate to allow input to the computing engine 300 or to provide output from the computing engine 300, respectively. The computing engine 300 may be implemented in hardware, software or a combination of hardware and software.

Figure 4:
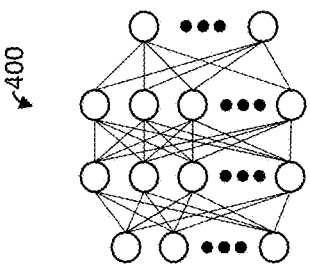
FIG. 4 depicts an exemplary simple deep learning model that may be utilized to implement the disclosed embodiments.

The computing engine 300 may generally operate to support one or more deep learning models. FIG. 4 depicts an exemplary simple deep learning model 400 that may be utilized to implement the disclosed embodiments. While a simple deep learning model is shown, it should be understood that the disclosed embodiments may be implemented utilizing a deep learning model including one or more gated recurrent units (GRUs), long short term memory (LSTM) networks, fully convolutional neural networks (FCNs), generative adversarial networks (GANs), back propagation (BP) neural networks, radial basis function (RBF) neural networks, deep belief nets (DBN) neural networks, Elman neural networks, attention neural networks, or any deep learning model capable of performing the operations described herein. It should also be understood that the different functions of the disclosed embodiments may be implemented with a deep learning model with parameters shared among the different operations performed by the deep learning model.

The deep learning model 400 may be trained to map low resolution to high resolution image slices with self supervision by ensuring a consistency between the original and downsampled image slices, between the switched dimension increased resolution image slices and the increased resolution downsampled switched dimension image slices, and between the downsampled switched back increased resolution image slices and the original image slices.

The computing engine 300 may also provide a platform for the computational framework. For example, the computational framework may include a combination of software, hardware, processors, and memory that may operate to manipulate and process image slices as described herein under control of the computer readable program code, and may be integrated within the hardware and software of the computing engine 300.

Figure 5:
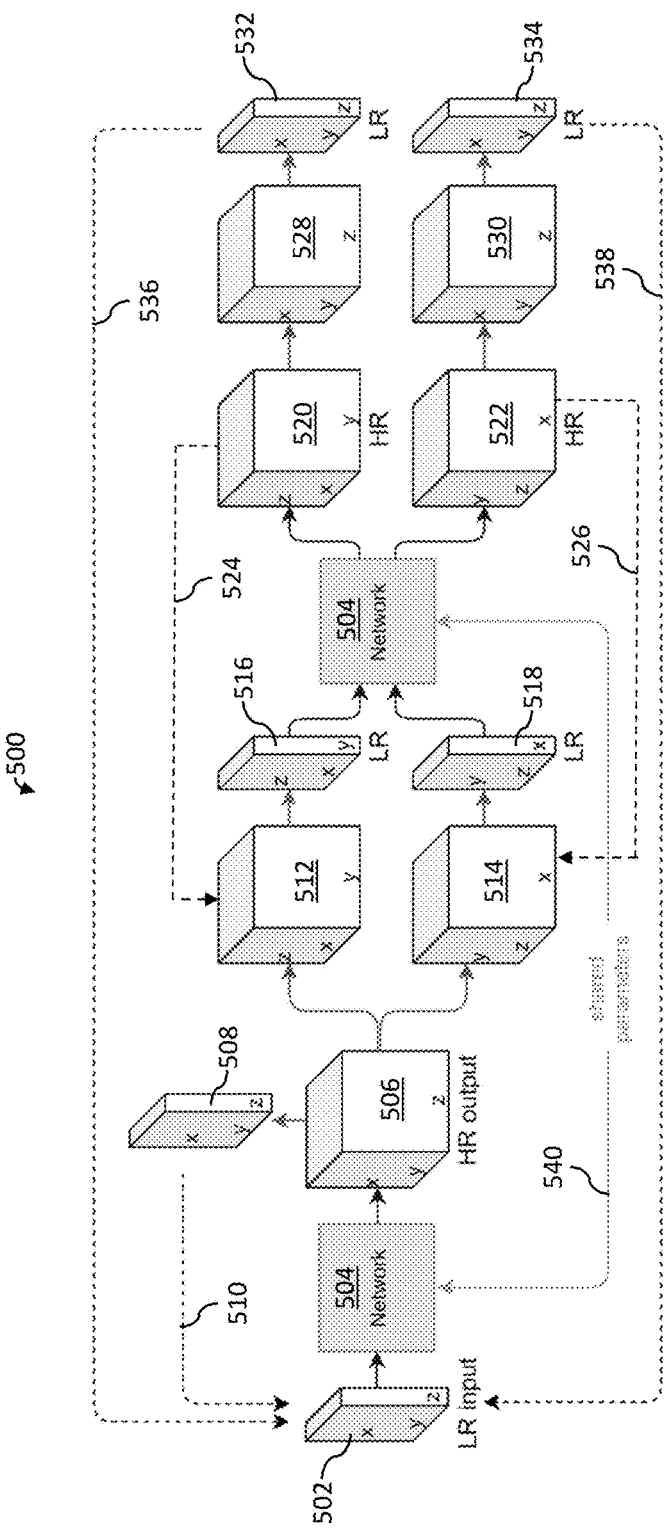
FIG. 5 shows a detailed flow diagram of a process for providing unsupervised interslice super resolution medical images.

FIG. 5 shows a detailed flow diagram of the computational framework 500 for optimizing the deep neural network with self-supervised learning where it is trained to map an interslice low resolution medical image to an interslice high resolution medical image under self-supervision constraints, according to the disclosed embodiments. A plurality of low resolution (LR) image slices 502, defined as having Z dimensions in the interslice direction with lower resolutions than X and Y dimensions in the intraslice directions, are provided to a deep learning model, referred to here as a network 504. The network 504 operates to up sample the LR image slices 502 to produce image slices with an increased resolution in the Z dimension 506, by using an adjustable mathematical mapping. The image slices with an increased resolution in the Z dimension 506 are downsampled in the Z dimension to produce LR downsampled image slices 508 with the same size as the LR image slices 502. The computational framework calculates first self-supervision losses 510 by measuring differences between the downsampled image slices 508 and the LR image slices 502. The network 504 learns to map the LR image slices 502 to the increased resolution image slices 506 by extracting features in the LR image slices 502 and modifying the mathematical mapping to minimize the first self-supervision losses 510 and uses the modified mathematical mapping to modify the image slices with an increased resolution in the Z dimension 506.

The dimensions of the modified image slices with an increased resolution in the Z dimension 506 are rotated or switched to synthesize image slices with an increased resolution in the Z dimension with an interslice direction in the Y dimension 512 and synthesize image slices with an increased resolution in the Z dimension with an interslice direction in the X dimension 514. The image slices with an interslice direction in the Y dimension 512 are downsampled in the Y dimension to produce LR image slices with an interslice direction in the Y dimension 516, and LR image slices with an interslice direction in the X dimension 518. The LR image slices with an interslice direction in the Y dimension 516, and the LR image slices with an interslice direction in the X dimension 518 are upsampled to produce HR image slices with an interslice direction in the Y dimension 520, and HR image slices with an interslice direction in the X dimension 522. The network 504 learns to map the downsampled resolution increased image slices 516, 518 to the resolution increased image slices 512, 514 by extracting features in the downsampled resolution increased image slices 516, 518 and minimizing the second self-supervision losses 524, 526 that measure the difference between its output 520, 522 and the resolution increased image slices 512, 514.

The dimensions of the HR image slices with an interslice direction in the Y dimension 520 are rotated or switched to an orientation with intraslice X and Y dimensions and interslice Z dimensions 528, and the resulting image slices are downsampled to produce LR downsampled image slices 532 with the same size as the LR image slices 502. The network 504 learns to minimize the third self-supervision losses 536, 538 that measure differences between the LR image slices 532, 534 and LR image slices 502.

It should be noted that deep learning model parameters adjusted as a result of the feature learning and the self-supervision loss minimizations are shared 540 across the different operations performed by the network 504.

It also be noted that in the event that high resolution images are available as a training ground truth, for example, from a different kind of modality, it should be understood that low resolution images may be synthesized by down-sampling in the Z dimension and using the corresponding high and low resolution images as training pairs to pre-train the network 504.

Thus, while there have been shown, described and pointed out, fundamental novel features of the invention as applied to the exemplary embodiments thereof, it will be understood that various omissions, substitutions and changes in the form and details of devices and methods illustrated, and in their operation, may be made by those skilled in the art without departing from the spirit and scope of the presently disclosed invention. Further, it is expressly intended that all combinations of those elements, which perform substantially the same function in substantially the same way to achieve the same results, are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method comprising:
  acquiring first 3D image slices with interslice resolutions lower than intraslice resolutions;
  upsampling the first 3D image slices to produce second 3D image slices with increased interslice resolutions by using an adjustable mathematical mapping;
  downsampling the second 3D image slices;
  calculating first self-supervision losses by measuring differences between the downsampled image slices and the first 3D image slices;
  modifying the mathematical mapping to minimize the first self-supervision losses;
  using the modified mathematical mapping to modify the second 3D image slices; and
  providing the modified second 3D image slices to a user through a user interface.

2. The method of claim 1, further comprising downsampling the modified second 3D image slices to dimensions of the first 3D image slices.

3. The method of claim 1, further comprising:
  switching dimensions of the modified second 3D image slices to produce third 3D image slices;
  downsampling the third 3D image slices to dimensions of the first 3D image slices;
  upsampling the downsampled third 3D image slices to produce fourth 3D image slices using the adjustable mathematical mapping;

calculating second self-supervision losses by measuring differences between the fourth and third 3D image slices; and adjusting the adjustable mathematical mapping to minimize the second self-supervision losses.

4. The method of claim 3, wherein switching dimensions of the second 3D image slices produces the third 3D image slices with interslice resolutions matching the intraslice resolutions of the first 3D image slices.

5. The method of claim 3, wherein upsampling the downsampled third 3D image slices produces the fourth 3D image slices with dimensions of the third 3D image slices.

6. The method of claim 3, further comprising:

switching dimensions of the fourth 3D image slices to produce fifth 3D image slices;

downsampling the fifth 3D image slices to produce sixth 3D image slices;

calculating third self-supervision losses by measuring differences between the sixth 3D image slices and the first 3D image slices; and adjusting the mapping to minimize the third self-supervision losses.

7. The method of claim 6, wherein switching dimensions of the fourth 3D image slices produces the fifth 3D image slices with intraslice and interslice axes matching intraslice and interslice axes of the first 3D image slices.

8. The method of claim 6, wherein downsampling the fifth 3D image slices produces the sixth 3D image slices with dimensions of the first 3D image slices.

9. The method of claim 1, further comprising using a deep neural network to formulate the mathematical mapping for reconstructing the second 3D image slices from the first 3D image slices and reconstructing the fourth 3D image slices from the downsampled third 3D image slices.

10. The method of claim 9, wherein the deep neural network comprises one or more gated recurrent units, long short term memory networks, fully convolutional neural network models, generative adversarial networks, back propagation neural network models, radial basis function neural network models, deep belief nets neural network models, and Elman neural network models.

11. A system comprising:

a source of first 3D image slices with interslice resolutions lower than intraslice resolutions;

a deep neural network configured to upsample the first 3D image slices to produce second 3D image slices by extracting features in the first 3D image slices;

a computational framework for optimizing the deep neural network configured to:

downsample the second 3D image slices;

calculate first self-supervision losses by measuring differences between the downsampled image slices and the first 3D image slices; and optimize the deep neural network to minimize the first self-supervision losses; and a user interface for providing the third 3D image slices to a user.

12. The system of claim 11, wherein upsampling the first 3D image slices produces the second 3D image slices with increased interslice resolutions.

13. The system of claim 11, wherein the computational framework is further configured to downsample the second 3D image slices to dimensions of the first 3D image slices.

14. The system of claim 11, wherein the computational framework is further configured to:

switch dimensions of the second 3D image slices to produce third 3D image slices; and downsample the third 3D image slices to dimensions of the first 3D image slices.

15. The system of claim 14, wherein switching dimensions of the second 3D image slices produces the third 3D image slices with interslice resolutions matching the intraslice resolutions of the first 3D images.

16. The system of claim 11, wherein the deep neural network is further configured to upsample the downsampled third 3D image slices to produce fourth 3D image slices by extracting features in the downsampled fourth 3D image slices.

17. The system of claim 16, wherein upsampling the downsampled third 3D image slices produces the fourth 3D image slices with dimensions of the third 3D image slices.

18. The system of claim 14, wherein the computational framework is further configured to:

calculate second self-supervision losses by measuring differences between the fourth and third 3D image slices;

switch dimensions of the fourth 3D image slices to produce fifth 3D image slices;

downsample the fifth 3D image slices to produce sixth 3D image slices;

calculate third self supervision losses by measuring differences between the sixth 3D image slices and the first 3D image slices; and optimize the deep neural network to minimize the second and third self-supervision losses.

19. The system of claim 18, wherein switching dimensions of the fourth 3D image slices produces the fifth 3D image slices with intraslice and interslice axes matching intraslice and interslice axes of the first 3D image slices.

20. The system of claim 18, wherein downsampling the fifth 3D image slices produces the sixth 3D image slices with dimensions of the first 3D image slices.

* * * * *